United States Patent [19]

Portner et al.

[11] 4,265,241
[45] May 5, 1981

[54] IMPLANTABLE INFUSION DEVICE

[75] Inventors: Peer M. Portner, Kensington; Jal S. Jassawalla, San Francisco, both of Calif.

[73] Assignee: Andros Incorporated, Berkeley, Calif.

[21] Appl. No.: 15,927

[22] Filed: Feb. 28, 1979

[51] Int. Cl.³ .............................................. A61M 7/00
[52] U.S. Cl. ............................. 128/260; 128/DIG. 12
[58] Field of Search ............... 128/213, 214 E, 214 F, 128/DIG. 12, DIG. 13, 260; 3/1

[56] References Cited

U.S. PATENT DOCUMENTS

| | | | |
|---|---|---|---|
| 3,527,220 | 9/1970 | Summers | 128/260 |
| 3,659,600 | 5/1972 | Merrill | 128/260 X |
| 3,692,027 | 9/1972 | Ellinwood, Jr. | 128/260 |
| 3,731,681 | 5/1973 | Blackshear et al. | 128/260 X |
| 3,894,538 | 7/1975 | Richter | 128/260 |
| 3,923,060 | 12/1975 | Ellinwood, Jr. | 128/260 |
| 3,951,147 | 4/1976 | Tucker et al. | 128/260 |
| 4,003,379 | 1/1977 | Ellinwood, Jr. | 128/260 |
| 4,013,074 | 3/1977 | Siposs | 128/260 |
| 4,056,095 | 11/1977 | Rey et al. | 128/260 X |

Primary Examiner—John D. Yasko
Attorney, Agent, or Firm—Fitch, Even, Tabin, Flannery & Welsh

[57] ABSTRACT

Multiple embodiments of an implantable infusion device for delivering precisely regulated dosages of drugs are disclosed, each device including reservoir means for containing the drug, catheter means for delivering the drug to the body and an actuating means which is responsive to a signal applied externally of the body for initiating delivery of a precisely regulated dosage. In one embodiment, the device is implanted subcutaneously to permit actuation by a solenoid driven element responsive to coded telemetry signal applied through the skin. In additional embodiments, the reservoir is pressurized for example, by means of vapor pressure or a mechanical spring, the drug under pressure in the reservoir being released in response to an externally applied signal.

4 Claims, 8 Drawing Figures

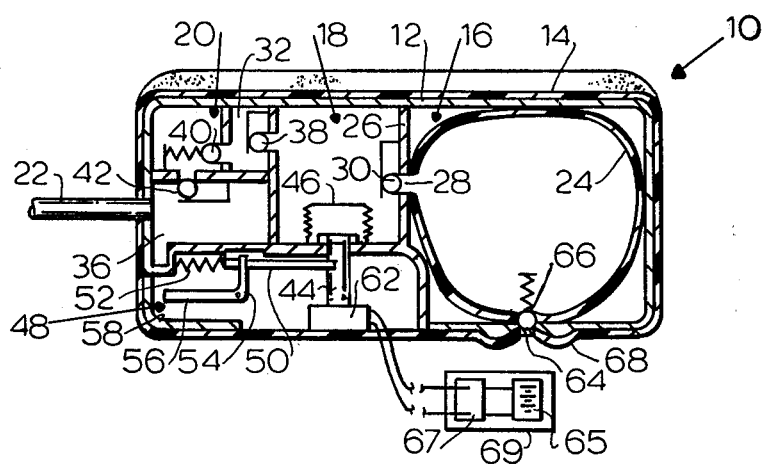
FIG. 1
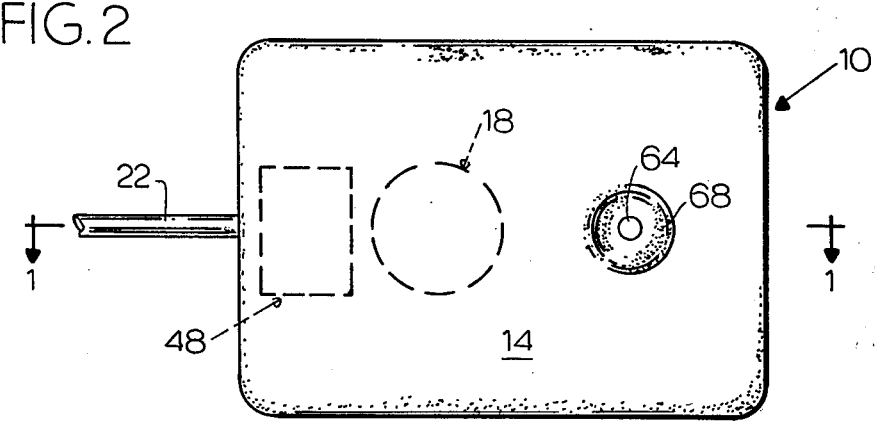
FIG. 2
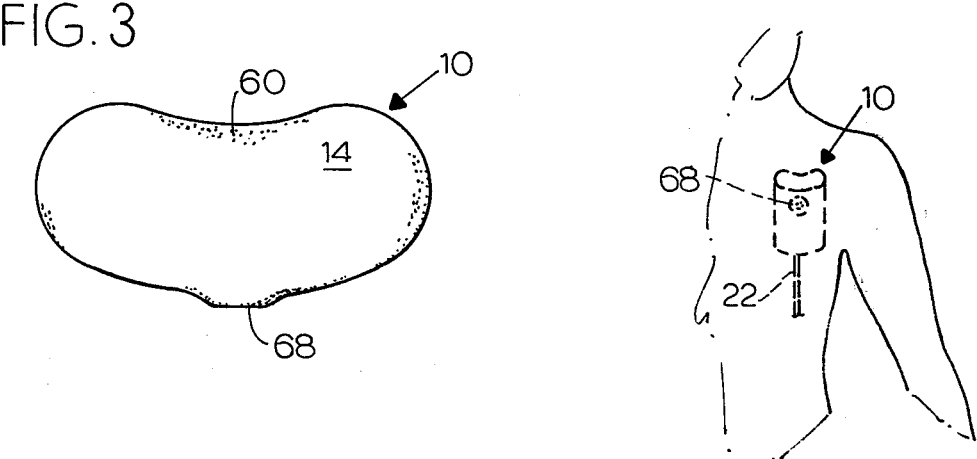
FIG. 3
FIG. 4

IMPLANTABLE INFUSION DEVICE

The present invention relates to drug delivery systems and more particularly to drug infusion devices which are implanted within the body of a patient.

Various types of drug delivery systems are well known in the prior art. Possibly the most common of these systems has been employed for the delivery of drugs to bedridden patients using an elevated container with a valve controlling the drip rate of the drug into a tube coupled with a needle inserted into the patient's body. With such a system, the flow rate may be controlled by means of the valve and may be readily monitored by visual observation of the drip rate. These systems present a number of problems, not the least of which is their limitation for use only with bedridden patients.

Other types of drug delivery systems are also known which employ various types of flow control devices. For example, a drug may be delivered by operation of a low volume pump. All of these systems as employed within the prior art have exhibited numerous shortcomings. For example, most systems employing pumps have been rather large and have required substantial amounts of power for proper operation. In addition, these devices are typically limited to use with bedridden patients.

Certain drug delivery systems have been considered for complete implantation within the body of a patient. Possibly, the most common type of device employed in this manner in the prior art has included a permeable membrane for controlled diffusion of a drug into the body from a suitable reservoir. However, such devices are limited in application primarily since the rate at which the drug is delivered to the body is completely dependent upon the rate of diffusion through the permeable membrane. Once the device is implanted within the body, external control over the device is no longer possible. Accordingly, the rate of drug delivery to the body may be affected by differing conditions within the body. In addition, such systems make no provision for the adjustment of the rate or time interval for drug delivery.

Accordingly, there has been found to remain a need for an effective drug delivery system which may readily be employed particularly by ambulatory patients while permitting precise and preferably variable control over the rate of drug delivery to the body.

Accordingly, it is an object of the present invention to provide a drug delivery system including an infusion device which is totally implantable within the body of a patient while being responsive to a signal generated externally of the patient's body for causing a precisely regulated dosage of the drug to be delivered to a selected portion of the body.

Within the various preferred embodiments of the invention, the drug is maintained within a suitable reservoir formed as a portion of the implantable device along with a catheter providing communication to a selected portion of the patient's body. In addition, the invention contemplates the inclusion of actuating means along with the implantable device, the actuating means being responsive to a signal generated or applied externally of the patient's body for causing a precisely regulated dosage of a selected drug to be delivered to the body through the catheter.

In one embodiment of the invention, the implantable infusion device may be actuated by a telemetry signal applied to activate a solenoid powered by an implanted battery. With such a device, the rate and interval for drug delivery to the body may be selectively controlled even with the device being completely implanted within the body.

Even more preferably, it is desirable to prevent accidental actuation of the device except when it is specifically intended to cause a selected dosage of drug to be delivered into the body. For this reason, the device also preferably includes a safety latch means normally preventing delivery of the drug into the body, for example through the catheter noted above. The safety latch means is also responsive to a signal generated or applied externally of the body for selectively permitting drug delivery. In order to assure against accidental actuation of the device, the safety latch means is more preferably responsive to a signal different from that applied for operating the actuating means. With such an arrangement, it is necessary to apply separate selected signals both for releasing the safety latch means and for operating the actuating mechanism of the device in order to cause the delivery of a selected drug dosage through the catheter.

In other embodiments of the drug infusion device, the drug is pressurized within the reservoir, for example, by means of vapor pressure developed within a separate chamber adjacent the reservoir or through a suitable spring assembly, release of the pressurized drug into the body then being regulated by means such as a solenoid valve or the like in response to an externally applied signal. With such a combination, a specifically coded telemetry signal may be used for actuation of the solenoid valve in order to assure against accidental or undesired release of the drug to the body. However, even with drug infusion devices of this type, it is possible to also employ additional safety latch means responsive to a separate signal in order to even more positively assure that the drug is delivered to the body only when intended.

Such a device is contemplated to have numerous applications for delivery or administration of drugs to the body. For example, it is particularly contemplated that such a device or method could be employed to provide an artificial pancreas for delivering insulin into the body with both the rate and interval of drug administration being selectively controlled externally of the body. Numerous other applications for such a device will be apparent from the following description of the preferred embodiments.

FIG. 1 is a sectioned view illustrating internal construction of one embodiment of an implantable infusion device including mechanical actuating means for regulating drug delivery, the view of FIG. 1 being taken along section line I—I of FIG. 2.

FIG. 2 is a plan view of the drug delivery or infusion device of FIG. 1.

FIG. 3 is an end view of the infusion device of FIG. 1.

FIG. 4 is a view illustrating subcutaneous implantation of the device of FIG. 1.

Figure 5:
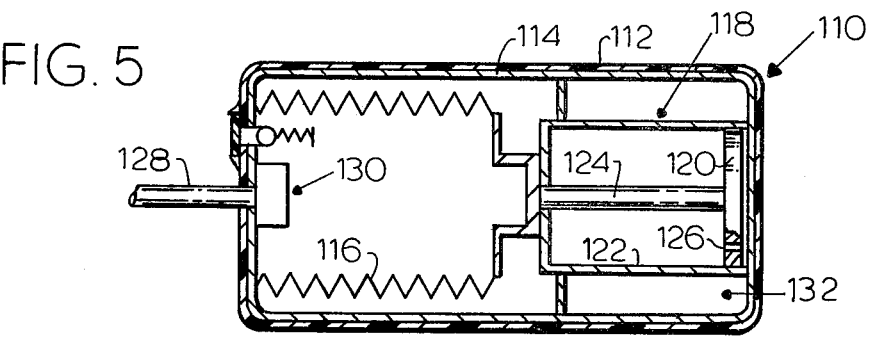
FIG. 5 is a sectioned view generally similar to FIG. 1 while illustrating yet another embodiment of an implantable infusion device according to the present invention wherein a drug is maintained under pressure by operation of a gas cylinder and released to the body by actuation of a solenoid in response to an externally generated signal.

As summarized above, the method and apparatus of the present invention is described below in connection with four specific embodiments illustrated respectively in FIGS. 1–3, 5, 6 and 7.

Each of these embodiments provides a drug infusion device or delivery system which may be completely implanted within the body of a patient to deliver a selected drug to the body. Most importantly, both the rate and interval of drug delivery to the body may be selectively controlled by an actuating signal generated or applied externally of the body. Accordingly, each of the four embodiments demonstrates means for carrying out a method of selectively releasing precisely regulated dosages of a drug to the body of a patient from a reservoir implanted within the body but in response to a signal generated or applied externally of the body. As noted above, the embodiment of FIGS. 1–3 comtemplates application of a coded telemetry actuating signal directly through the skin, to cause energization of a solenoid from an implanted battery. In each of the embodiments of FIGS. 5–7, the drug is placed under pressure within a reservoir of the device while its rate and interval of release from the device is regulated by suitable means, preferably a solenoid valve, in response to an externally generated signal, preferably a coded telemetry signal.

In describing the embodiments of FIGS. 1–3 in greater detail, having reference to those FIGURES, an implantable infusion device is generally indicated at 10 and includes a rigid housing 12 preferably formed from stainless steel or titanium. The stainless steel or titanium housing 12 is encased with a sheath 14 of a material designed for compatibility with the body, preferably a biocompatible polymer such as silicone rubber or polyurethane.

The interior of the housing 12 is generally divided into three regions including a reservoir portion 16, a pumping chamber portion 18 and an outlet portion 20 arranged for communication with a catheter 22 which is disposed outside of the housing 12. The entire housing 12 is also slightly curved as may be best seen in FIG. 3 in order to better adapt the device to the body configuration when it is implanted in the manner shown for example in FIG. 4.

The reservoir portion 16 of the device is separately formed by the housing 12 and further includes a distendible bladder 24 for containing a selected drug. A metal bellows could also be used for the same purpose. A wall portion 26 of the housing 12 which is arranged between the reservoir 16 and pumping chamber 18 forms an opening 28 with the interior of the bladder 24 being in communication with the pumping chamber 18 through the opening. However, the opening is normally closed by an inlet check valve 30 which operates in a manner described in greater detail below to regulate communication of the fluid drug in the bladder into the pumping chamber.

The housing 12 also includes internal structure forming a plurality of outlet chambers providing serial communication between the pumping chamber and the catheter. The outlet chambers are indicated respectively at 32, 34 and 36, the outlet chamber 36 being a final chamber which is in direct communication with the catheter 22. A separate outlet check valve respectively regulates communication of a drug from the pumping chamber into the first outlet chamber 32, from the outlet chamber 32 into the next chamber 34 and from the chamber 34 into the final outlet chamber 36 and accordingly into the catheter 22. The check valves are indicated respectively at 38, 40 and 42. Preferably, one of the check valves, indicated at 40, is of a separate type or design in order to better assure operation of the serial arrangement of check valves under all conditions.

Actuation of the device is accomplished by means of a mechanical plunger 44 which is arranged outside of the housing 12 so that an actuating force may be directly applied to the plunger. The plunger extends through an opening in the housing 12 into the pumping chamber where it is connected with a piston bellows 46. Thus, mechanical actuation or depression of the plunger tends to pressurize the pumping chamber causing the flow of a drug through the check valves 38–42 and into the catheter. Upon release of the plunger, it is urged into its extended position as illustrated in FIG. 1 by spring action of the piston bellows. In this manner, the volume of the pumping chamber is again diminished so that fluid drug from the bladder 24 passes through the inlet check valve 30 to again fill the pumping chamber.

As indicated above, it is particularly desirable to assure that operation of the infusion device takes place only when properly intended. Accordingly, a safety latch assembly 48 is provided which prevents operation of the device unless separate externally generated or applied signals are caused to operate both the safety latch assembly 48 and the plunger 44.

The safety latch assembly could take many different forms. For example, it might be in the form of a valve blocking communication from the final outlet chamber 36 into the catheter. However, the safety latch assembly 48 is preferably a mechanical latching unit for preventing movement of the plunger 44 except when two separate actuating signals are applied as described above. For this reason, the safety latch assembly 48 includes a plunger latching member 50 which is urged into locking engagement with the plunger 44 by means of a latch spring 52. An unlatching paddle 54 is formed as a bellcrank coupled with the unlatching paddle 54 and having a magnetic arm 56.

A magnetic signal may thus be applied to the magnetic arm when the device is implanted within the body for causing the latching member 50 to shift against the spring 52 and thereafter permits mechanical operation of the plunger 44. The housing around the safety latch is formed from a non-magnetic material such as stainless steel or plastic with a rigid extension 58 extending outwardly around the safety latch assembly 48. As noted above, the plunger 44, is covered only by the elastic coating 14 to permit its mechanical actuation. As an alternative, the latch may be operated by a suitable device such as a solenoid (not shown) operated by a control (not shown) responsive to a telemetry signal generated outside the body.

Referring momentarily to FIGS. 1-3 in combination, it may be seen that the overall configuration of the device includes a convex side 60 (FIG. 3) upon which side the plunger 44 has a solenoid 62 positioned to cause axial movement of the plunger in response to signals applied to the solenoid. The solenoid is powered from a battery 65, controlled by a telemetry receiver 67 of suitable design. The battery 65 and receiver 67 are implantable and are completely covered by a sheath 69 of biocompatible material. As an alternative, the battery 65 and receiver 67 may be enclosed within the sheath 14.

On the same side of the device, the housing 12 forms an additional opening 64 through which the drug supply within the bladder 24 may be replenished. An additional check valve 66 is arranged within the opening 64 to permit a fluid drug to be injected into the bladder while preventing the drug from escaping out of the bladder through the opening 64. The coating 14 for the housing thus forms a resealable septum above the opening 64 allowing a needle to be inserted through the skin, the coating septum and the opening 64 for injecting a fresh supply of drugs into the reservoir or bladder 24. Upon retraction of the needle, the opening 64 is again closed by the check valve 66 so that the drug may be supplied to the body only by proper operation of the plunger and latching assembly as described above. The housing 12 is also formed with an annular ridge 68 surrounding the opening 64 in order to assist in location of the opening 64 for injection of the drug into the reservoir.

In operation of the embodiment of FIG. 1, the device is subcutaneously implanted within the body as illustrated in FIG. 4 with the housing opening 64 being exposed just beneath the skin. A fresh supply of drug is injected into the reservoir or bladder through the opening 64 and check valve 66 as described above. The drug within the bladder is placed under constant pressure, preferably by means of a fluid such as Trichloroflouromethane $CCL_3F$ (Freon II (TM) -DuPont) for example and disposed within the housing about the bladder 24. At body temperature, vaporization of the fluid tends to exert a limited but constant positive pressure upon the bladder.

As indicated above, operation of the plunger 44 is accomplished by external application of a magnetic signal upon the safety latch assembly 48 followed by the application of a telemetry signal to actuate the plunger 44. The plunger may be actuated one or more times to cause a carefully regulated volume or dosage of drug from the pumping chamber to pass through the outlet chambers 32-36 and the check valves 38-42 into the catheter 22 for delivery to the body. As fluid is expelled from the pumping chamber by depression of the plunger, additional drug passes into the pumping chamber from the bladder by operation of the inlet check valve 30 when the plunger is again retracted.

Thus, a relatively large dosage of drugs may be implanted within the body and assured against undesired delivery to the body except by externally controlled operation of the infusion device in the manner described above.

Figure 6:
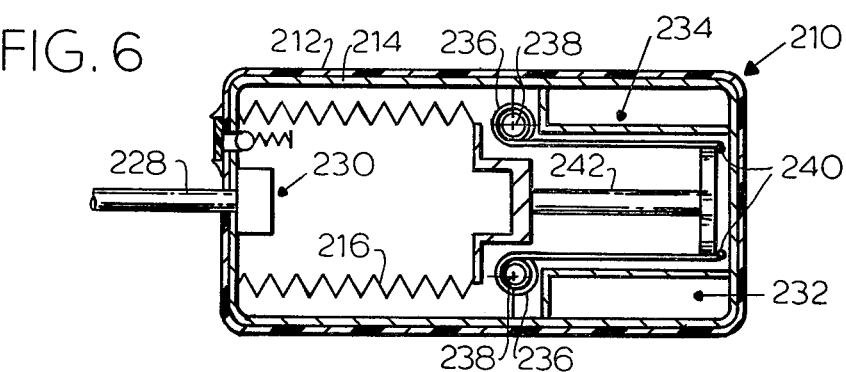
FIG. 6 is a similarly sectioned view of yet another embodiment of an implantable infusion device according to the present invention wherein the drug is pressurized by mechanical spring means and similarly released by operation of a solenoid valve.
Figure 7:
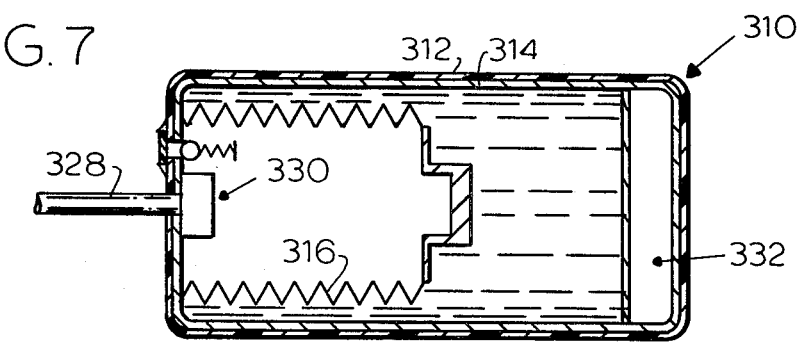
FIG. 7 is also a sectioned view of yet another embodiment of an implantable infusion device according to the present invention wherein the drug is pressurized by a fluid saturated at body temperature, the pressurized drug being released to the body by actuation of a solenoid valve.

Unlike the embodiment of FIGS. 1-3, each of the embodiments of FIGS. 5-7 includes different means for placing a reservoir of a selected drug under pressure with outlet means such as a solenoid valve being operable in response to an externally applied signal for releasing closely regulated dosages of the drug to the body.

Referring first to FIG. 5, another embodiment of an implantable infusion device is indicated at 110 and includes a housing 112 which may be covered by a coating 114 generally similar to that indicated at 14 in FIG. 1. A drug reservoir is formed adjacent one end of the housing 112 by a bellows 116.

Pressure is applied to the drug within the bellows by means of a gas spring cylinder assembly 118 comprising a piston 120 slidably arranged within a cylinder 122 and connected to a rod 124 which is also secured to the collapsible bellows 116. The piston 120 has a small hole 126 which permits equalization of pressure upon both sides of the piston. The cylinder is filled with a suitable inert gas such as nitrogen or argon. The piston is urged leftwardly within the cylinder, as viewed in FIG. 5, because of the differential effective area of the piston formed by the rod 124. The variation in pressure acting on the drug as the drug is used up is compensated by adjusting the "open" duration of the solenoid valve.

Figure 8:
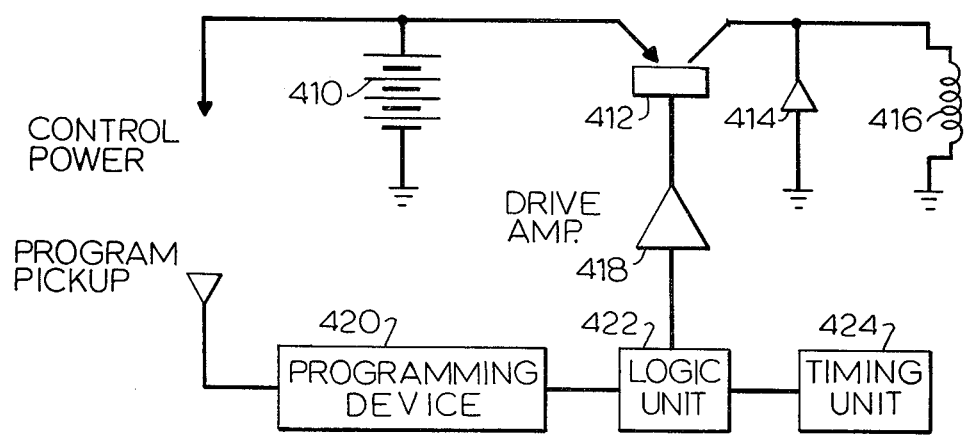
FIG. 8 is a schematic representation of suitable electronic circuitry for use in any of the embodiments of FIGS. 5–7 to control actuation of their respective solenoid valves.

A catheter 128 extending from the housing 112 is in communication with the drug reservoir formed by the bellows 116. Communication between the bellows reservoir and the catheter is regulated by suitable means such as a solenoid valve 130. The solenoid valve 130 normally limits communication of the drug from the bellows reservoir to the catheter. Electronic circuitry for actuating the solenoid valve 130 is indicated generally at 132 and is arranged peripherally about the gas spring cylinder assembly 118. A typical example of circuitry which might be employed within the device is illustrated in FIG. 8 and described in greater detail below. For the present, it is noted that the circuitry is responsive to an externally applied signal, preferably a coded telemetry signal for actuating the solenoid valve and causing a closely regulated dosage of the drug to be delivered to the body.

The dosage of drug delivered to the body is of course determined both by the size of the opening provided between the reservoir and the catheter by the solenoid valve as well as by the pressure developed upon the bellows by the cylinder assembly 118. The amount of time during which the solenoid valve 130 remains open can of course be closely established or may even be varied under the regulation of the circuitry 132 in order to deliver variable or constant dosage of drugs to the body as determined by the externally generated signal applied to the circuitry 132.

It is also noted in FIG. 5 that the undesired delivery of drugs to the body may be prevented by designing the circuitry 132 so that it only functions in response to a carefully coded telemetry signal. However, it would also be possible to employ a safety latching assembly generally of the type indicated at 48 in FIG. 1 to even further assure against undesirable delivery of a drug to the body. Here again, such a safety latch assembly could operate in response to a separate signal from that employed for actuation of the solenoid valve 130 through the circuitry 132.

Another embodiment of an implantable infusion device is indicated at 210 in FIG. 6 and is generally similar to the embodiment of FIG. 5. Accordingly, similar components of the device of FIG. 6 are indicated by corresponding numerical labels used in FIG. 5 but preceded by the digit "2". Generally, in FIG. 6, drug within the bellows reservoir is pressurized by means of a mechanical spring assembly 234 instead of the gas cylinder assembly of FIG. 5. The mechanical spring assembly 234 preferably includes a plurality of constant-force extendible coil springs 236. The axes 238 of the spring coils 236 are secured relative to the housing 212. The extended ends 240 of the spring coils are secured to a plunger 242 which acts upon the bellows 216. Thus, the spring coils tend to apply a low intensity, constant force to the bellows for developing a small positive pressure on the drug contained within the bellows reservoir. The solenoid valve 230 functions in response to circuitry 232 for regulating communication of the drug from the bellows reservoir into the catheter 228 for delivery into the body. Here again, a suitable example of circuitry employable within the device of FIG. 6 is described below and illustrated in FIG. 8.

The embodiment of FIG. 7 is also very similar to those described above in connection with FIGS. 5 and 6. Accordingly, similar components of the device 310 of FIG. 7 are indicated by similar numerals preceded by the digit "3". Within the embodiment of FIG. 7, fluid pressure is again employed within the housing 312 to develop a small but constant positive pressure upon the bellows 316 and the drug contained therein. However, the fluid pressure is merely developed within a cavity formed by the housing 312 so that the fluid pressure completely surrounds the bellows 316. Thus, the constant vapor pressure developed by the fluid at body temperature produces the pressure which acts upon the bellows 316. Here again, the solenoid valve 330 is actuated by the circuitry 332 for closely regulating the communication of the drug from the bellows reservoir into the catheter 328 for delivery to the body.

It is also noted that a safety latch assembly similar to that described at 48 in FIG. 1 could also be employed within the embodients of FIGS. 6 and 7. However, within the embodiments of FIGS. 5-7, such a safety latch assembly would have to be designed for limiting communication of the drug into the catheter rather than for acting as a mechanical detent in the manner illustrated in FIG. 1.

Before proceeding with a description of the control circuit illustrated in FIG. 8, it is again noted that within each of the embodiments of FIGS. 5-7, regulation over drug delivery to the body is particularly dependent upon operation of the solenoid valve indicated at 130, 230 or 330. Preferably, the solenoid valve is load matched to integral valve means, for example a needle valve (not shown), by means of a spring (also not shown) which results in quiet controlled solenoid closure without significant impact force. In addition, with such a solenoid valve, it may be operated by a minimum amount of energy permitting any of the devices of FIGS. 5-7 to operate over extended periods of time on conventional battery power. As was indicated above, in each of the embodiments of FIGS. 5-7, the drug is maintained under constant low pressure within a bellows reservoir, the solenoid valve serving as a "gate" to release the drug from the belows, reservoir for delivery to the body through the catheter.

Flow metering could be accomplished for example in either of two different ways by a solenoid valve. In the first, the solenoid valve would open and close with no substantial dwell period in its open condition, flow taking place during the opening and closing of the valve. The quantity or dosage of drug delivered to the body would be determined by the number of opening and closing cycles experienced by the valve. Alternatively, a bistable solenoid valve could be employed which would remain in an open condition for a predetermined period of time. Such a valve could possibly be opened either magnetically or mechanically. Release of the valve to its closed condition could then be accomplished electrically within the solenoid.

With any such arrangement, it is only necessary to provide circuitry to assure that the solenoid either remains open for a selected period of time to release a controlled drug dosage or that a solenoid valve having a natural frequency is caused to open and close through a selected number of cycles to accomplish delivery of a selected drug dosage. Circuits for accomplishing these functions are well known in the prior art and FIG. 8 is a schematic illustration of a simple circuit which could possibly be employed for regulating operation of the solenoid valve.

Referring now to FIG. 8, the control circuit which is also generally indicated in FIGS. 5-7 at 132, 232 or 332, comprises a battery 410, a transistor switch 412 for regulating operation of the normally closed solenoid valve, a diode 414 and a permanent magnet 416. Control components for regulating operation of the transistor switch 412 include a drive amplifier 418 for delivering to the switch 412 a signal produced by the other control components including a programming device 420, a logic unit 422, and a timing unit or clock 424. The programming device 420 is adapted to receive an externally generated or applied signal, preferably a coded telemetry signal.

In operation, when a coded signal is received by the programming device 420 and applied through the drive amplifier 418, the switch is actuated, causing current from the battery 410 to flow through the switch into the magnet 416 and to increase to a value determined primarily by the resistance of the magnet and the voltage of the battery. These components are selected so that the current is sufficient to operate the solenoid valves of any of FIGS. 5-7.

When the switch 412 is deactuated by termination of the signal from the drive amplifier 418, the current in the magnet flows through the diode 414 and decays according to the time constant of the magnet. When the current decays to the selected level, the solenoid valve again closes. In a preferred mode of operation, the logic unit 422 develops a pulse train of a series of short signals in response to the programming device 420, the signals from the logic unit being very short so that they are substantially less than the natural period of vibration for the armature (not shown) of the solenoid valve. With such an arrangement, all opening cycles of the solenoid valve would be established by the above noted natural period of vibration. The logic unit 422 would then be employed to generate the number of such pulses corresponding to a count previously stored in the programming device 420. Such a series of pulses would be produced for each programmed clock period established by the continuously operating timing unit 424.

Alternatively, in a single pulse mode, the transistor switch 412 could be turned on for a period to assure actuation of the solenoid valve. The current delivered to the magnet 416 could then be reduced to a load level sufficient for holding the valve in an open condition or else a series of current pulses could be delivered, each pulse being much shorter than the time constant of the magnet. With a relatively long time constant for the magnet, such pulses would cause little fluctuation of the effective current. Such an arrangement is a standard means for lowering the effective DC circuit voltage without high dissipation. In this mode of operation, such a reduced "holding current" would be maintained for a programmed number of clock pulses and as established by the timing unit 424 after which the logic unit 422 would terminate the signal through the drive amplifier 418 with the transistor switch 412 being closed to deactuate the solenoid valve.

It is believed apparent that numerous modifications and variations are possible within the scope of the present invention as defined by the various embodiments set forth above. Accordingly, the scope of the present invention is defined only by the following appended claims.

We claim:

1. An implantable infusion device for delivering precisely regulated dosages of drugs under external control, comprising
a housing for the infusion device which is completely implantable within the body of a patient,
said housing including a reservoir chamber and a compressable reservoir arranged in said reservoir chamber for containing a selected drug,
catheter means for connecting said reservoir with a portion of the body to which the drug is to be delivered, said housing including a pumping chamber having inlet means in communication with said reservoir and outlet means in communication with said catheter, and
actuating means operable for causing flow of a precise dosage of the selected drug from said reservoir through said catheter means to the body portion, said actuating means having at least a portion implanted in the body of the patient along with said housing and including a movable element operable reciprocally to vary the volume of said pumping chamber and a solenoid for driving said element, said reservoir chamber containing means for developing a pressure within said reservoir which exceeds that of said pumping chamber when said movable element increases the volume thereof, a power source for said solenoid, and telemetry means responsive to a telemetered signal from outside the body for actuating said solenoid from said power source.

2. The infusion device of claim 1 further comprising safety latch means engageable with said movable element for preventing undesired operation of said movable element.

3. The infusion device of claim 1 further comprising inlet means for permitting injection of a drug supply into said reservoir while the infusion device is implanted within the body of a patient.

4. The implantable infusion device of claim 1 wherein said housing includes a plurality of outlet chambers arranged in series between said pumping chamber and said catheter means, and check valve means for regulating communication between said pumping chamber and the first of said outlet chambers and between adjacent outlet chambers.

* * * * *